(12) United States Patent
Baron et al.

(10) Patent No.: US 6,261,254 B1
(45) Date of Patent: Jul. 17, 2001

(54) LEVER-STYLE DRAIN ASSEMBLY FOR URINE COLLECTION CONTAINER

(75) Inventors: Robert J. Baron, Covington; Richard Arndt, Acworth; Igor Blinow, Gainesville, all of GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/357,721

(22) Filed: Jul. 21, 1999

(51) Int. Cl.[7] .................................................... G02B 6/38
(52) U.S. Cl. .......................... 602/323; 604/317; 604/322
(58) Field of Search ................................ 604/322, 323, 604/326, 335, 340, 350, 327, 249, 250; 222/96, 105, 179, 181, 106, 214, 491, 494, 212; 251/7, 231

(56) References Cited

U.S. PATENT DOCUMENTS

| | | |
|---|---|---|
| 3,415,299 | 12/1968 | Hinman, Jr. et al. . |
| 4,055,179 * | 10/1977 | Manschot et al. .................... 604/322 |
| 4,114,640 | 9/1978 | Forman . |
| 4,324,348 | 4/1982 | Johnson et al. . |
| 4,564,127 | 1/1986 | Garabedian et al. . |
| 4,570,829 | 2/1986 | Allen . |
| 4,946,451 * | 8/1990 | Cianci .................................. 604/323 |
| 5,084,035 | 1/1992 | Salvadori et al. . |
| 5,429,624 * | 7/1995 | Coelho ................................. 604/323 |
| 5,573,138 | 11/1996 | Lin . |
| 6,132,407 * | 10/2000 | Genese et al. ....................... 604/327 |

* cited by examiner

Primary Examiner—Kim M. Lewis
(74) Attorney, Agent, or Firm—Kilpatrick Stockton, LLP

(57) ABSTRACT

A fluid collection bag and drain assembly comprises: a container having an interior chamber for collecting fluid. Mounted to the container is a compressible, resilient outlet tube having a passage in fluid communication with the interior chamber of the container. A housing surrounds the outlet tube, and the discharge end of the outlet tube is disposed to discharge fluid through the open lower end of the housing. A lever is pivotably mounted to the housing. A closure member extending from the lever is operative to clamp off the outlet tube when the lever is in a closed position and to permit the outlet tube to open when the lever is in an open position. A cover member is pivotably mounted to the housing and is normally operative to close the open lower end of the housing. The cover member is operatively linked to the lever such that when the lever is opened, the cover member is opened to uncover the open lower end of the housing concurrent with the outlet tube being permitted to open. In this manner the cover member prevents accidental contact with the discharge end of the outlet tube when fluid is not being discharged from the container.

6 Claims, 5 Drawing Sheets

Fig_1

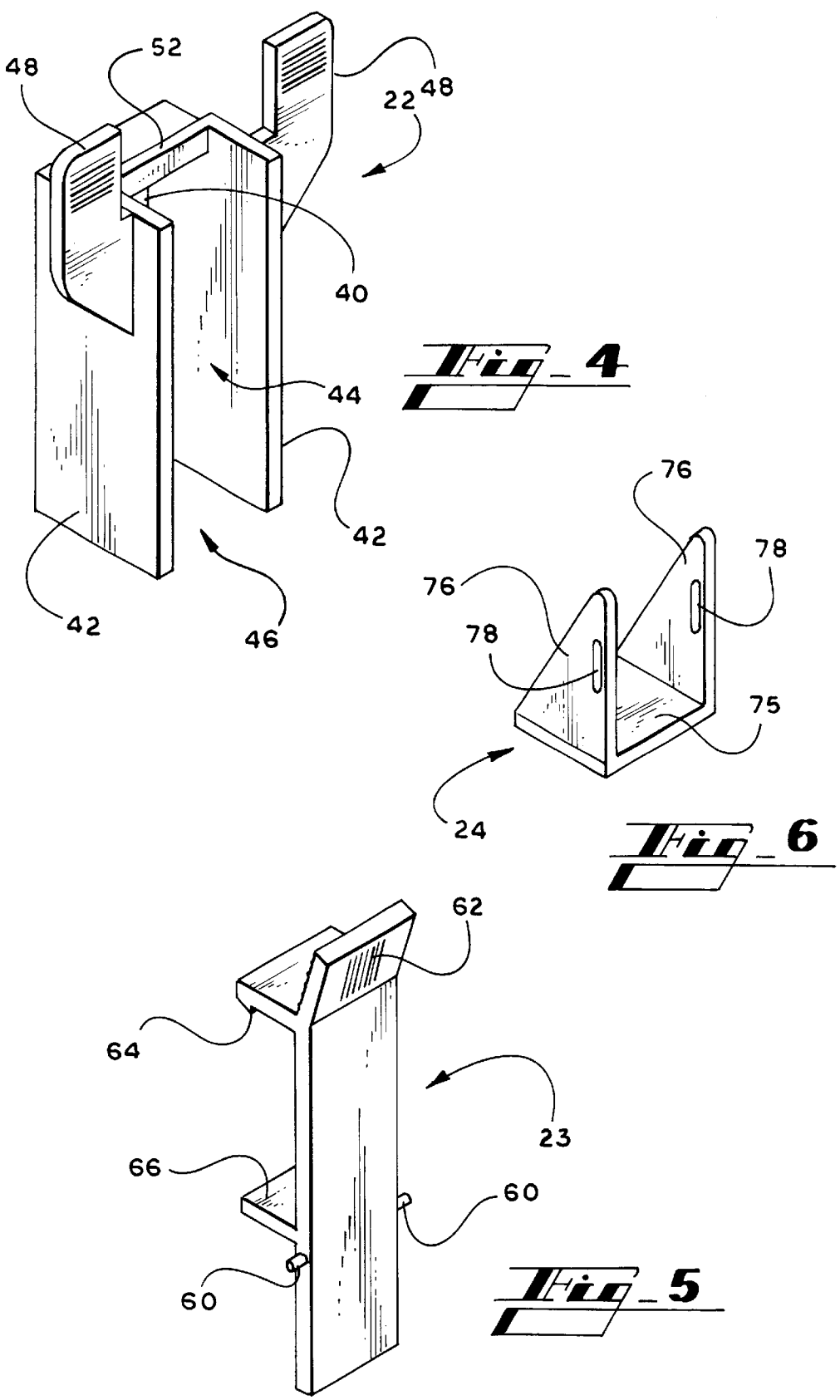

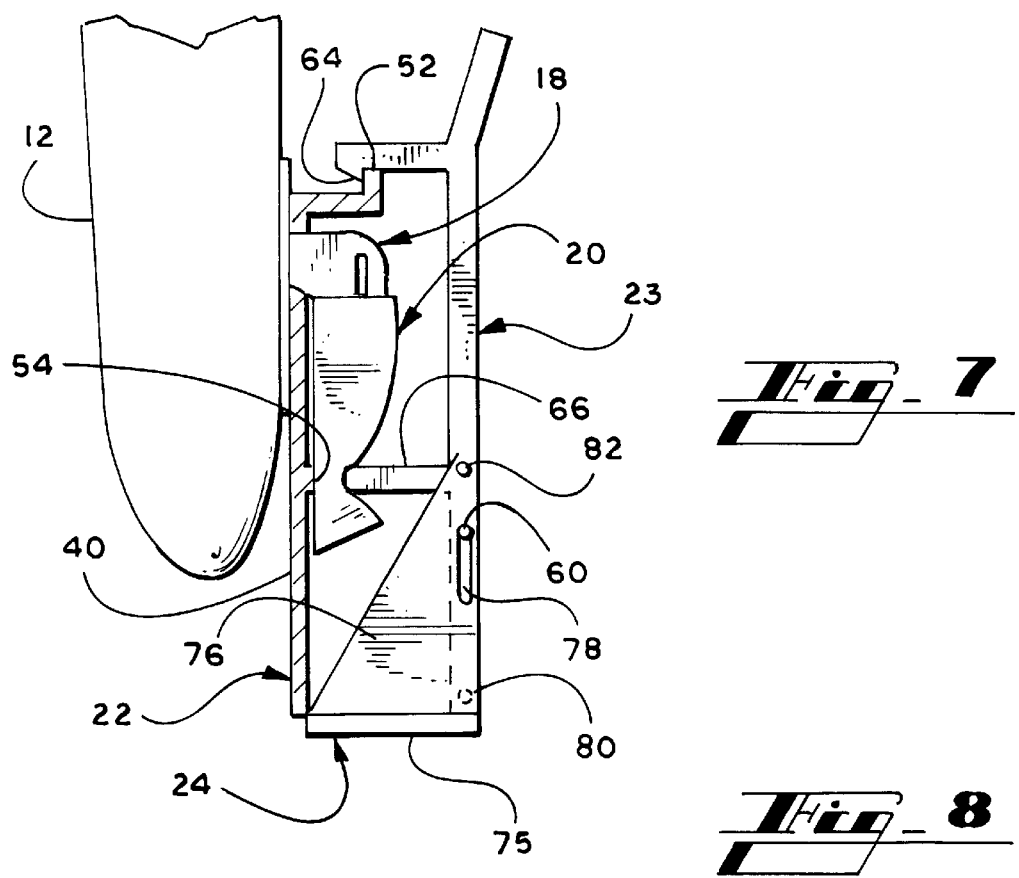
Fig_7
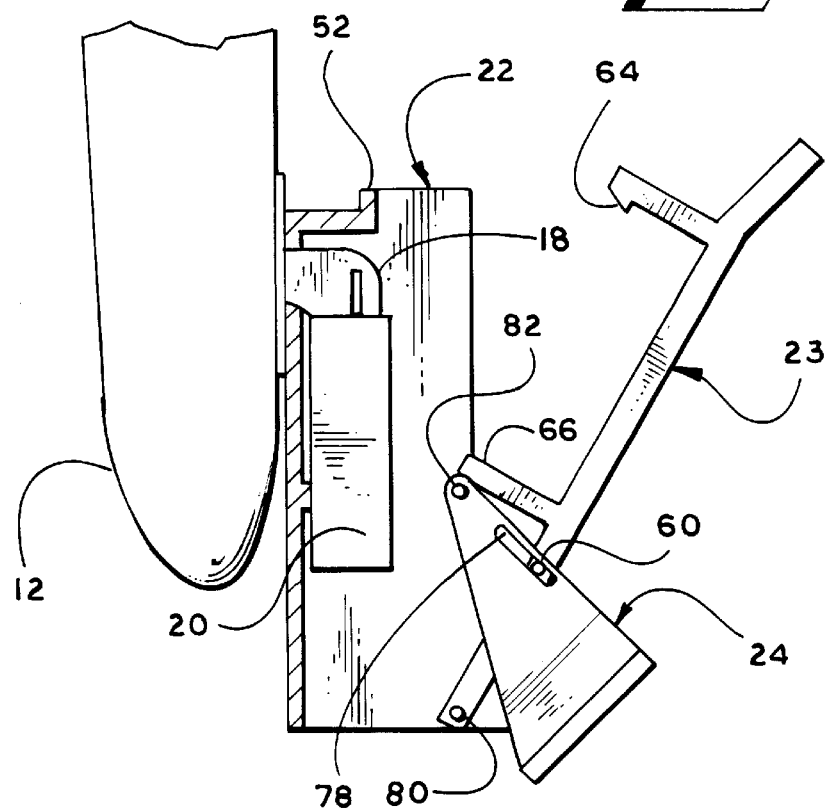
Fig_8

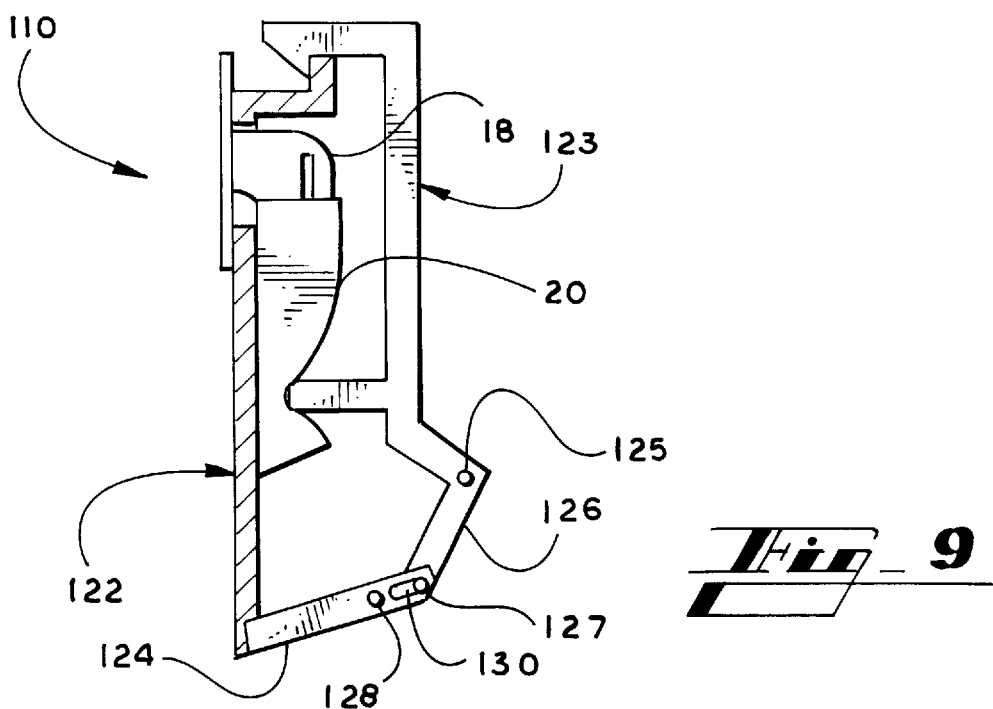
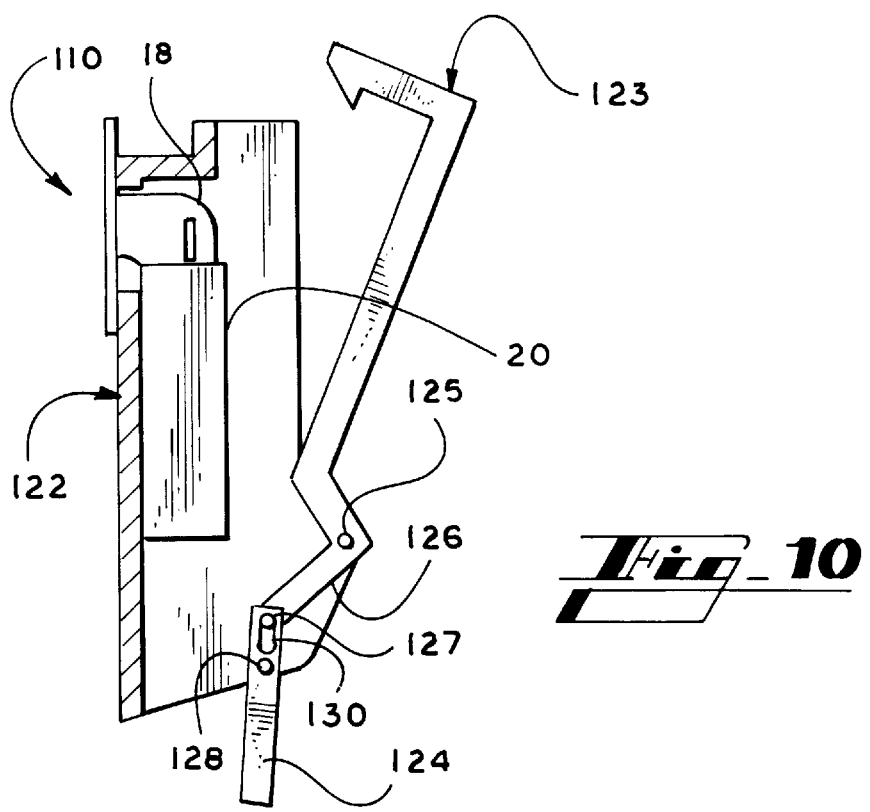

US 6,261,254 B1

LEVER-STYLE DRAIN ASSEMBLY FOR URINE COLLECTION CONTAINER

TECHNICAL FIELD

The present invention relates generally to urine collection containers and relates more specifically to a drain assembly for such a container.

BACKGROUND OF THE INVENTION

It is well known to discharge urinary catheters into urinary drainage bags for collecting urine from catheterized patients. Such bags are typically attached to the hospital bed below the level of the patient such that urine flows into the bag under force of gravity. To permit fluid to be drained from the bag, either when the bag becomes overly full or when a specimen is needed, a drain assembly is provided adjacent the lower end of the bag. Typically the drain assembly comprises a flexible, resilient outlet tube having one end in fluid communication with the interior of the bag. To prevent fluid from flowing through the outlet tube, some means for closing off the outlet tube is provided, such as a clamp which slides over the end of the tube and clamps the walls of the tube to occlude its lumen. Fluid is discharged through the outlet port by releasing the clamp from the outlet tube.

With the growing concern over the spread of diseases such as AIDS which are spread by contact with body fluids, it is important that the discharge end of the outlet tube be protected against accidental contact by attending healthcare personnel. At the same time, because urinary drainage bags must be attended by healthcare personnel who have many other duties, it is imperative that a urinary drainage bag be capable of being operated quickly, preferably a single step operation which can be accomplished with only one hand. Any means provided to prevent the attending healthcare personnel from accidentally contacting the contaminated discharge end of the outlet tube should not interfere with single step, single handed operation. Furthermore, because of the single-patient, disposable nature of urine collection bags, it is important that the urinary drainage bag be low cost and easy to manufacture.

Thus there is a need for an improved drain assembly for urinary collection bags.

There is a further need for a urinary drainage bag which has a drain assembly which protects attending healthcare personnel against accidental contact with the contaminated end of the discharge tubing.

There is also a need for a urinary drainage bag which has a drain assembly which operates quickly and easily, which requires only a single step to operate, and which can be operated with only one hand.

Finally there is a need for a urinary drainage bag which has a drain assembly which satisfies all of the foregoing needs while being inexpensive to manufacture.

SUMMARY OF THE INVENTION

Stated generally, the present invention comprises a urinary drainage bag which has a drain assembly which protects attending healthcare personnel against accidental contact with the contaminated end of the discharge tubing. The drainage bag of the present invention operates quickly and easily, requires only a single step to operate, and can be operated with only one hand. The drainage bag of the present invention provides all of these advantages while being inexpensive to manufacture.

Stated somewhat more specifically, the present invention comprises a fluid collection bag and drain assembly. A container has an interior chamber for collecting fluid. A compressible, resilient outlet tube is mounted to the container and has a passage in fluid communication with the interior chamber of the container. A housing surrounds the outlet tube and has an open lower end. The discharge end of the outlet tube is disposed to discharge fluid through the open lower end of the housing. A lever is pivotably mounted to the housing and has a closure member operative to clamp off the outlet tube when the lever is in a closed position and to permit the outlet tube to open when the lever is in an open position. A cover member is also pivotably mounted to the housing and is normally operative to close the open lower end of the housing. The cover member is operatively linked to the lever such that when the lever is opened, the cover member is opened to uncover the open lower end of the housing concurrent with the outlet tube being permitted to open. In the disclosed embodiment the cover member is operatively linked to the lever by means of a follower on the lever which rides within a cooperating slot in the lever. Thus the cover member prevents accidental contact with the discharge end of the outlet tube when fluid is not being discharged from the container.

Thus it is an object of the present invention to provide an improved drain assembly for urine collection containers.

It is another object of the present invention to provide a drain assembly for urine collection containers which can easily and reliably be operated with only one hand.

Still another object of the present invention is to provide a drain assembly for urine collection containers which provides the operator with control over the direction in which fluid is discharged, especially during opening and closing of the drain assembly.

Another object of the present invention is to provide a drain assembly for urine collection containers which is intuitive to operate.

Still another object of the present invention is to provide an outlet tube device which can be operated without the fingers and hands of the operator being in the proximity of the discharge tube so as to minimize or eliminate the possibility of transferring bacteria, fungus, or other contaminant from the operator's hands to the tube, where the contaminant could find its way into the bag and hence to the patient, or from the tube to the operator's hands, causing an unsanitary situation and exposing the operator to the possibility of infection or disease.

Other objects, features, and advantages of the present invention will become apparent upon reading the following specification, when taken in conjunction with the drawings and the appended claims.

Other objects, features, and advantages of the present invention will become apparent upon reading the following specification, when taken in conjunction with the drawings and the appended claims.

BRIEF DESCRIPTION OF THE DRAWINGS

FIG. 4 is a perspective view of the housing of FIG. 3.

FIG. 5 is a perspective view of a lever of the drain assembly of FIG. 1.

FIG. 6 is a perspective view of a cover member of the drain assembly of FIG. 1.

FIG. 7 is a side cutaway view showing the drain assembly of FIG. 1 in its closed position.

FIG. 8 is a side cutaway view showing the drain assembly of FIG. 1 in its open position.

FIG. 9 is a side cutaway view of an alternate embodiment of a drain assembly showing the drain assembly in its closed position.

FIG. 10 is a side cutaway view of the drain assembly of FIG. 9 showing the drain assembly in its open position.

DETAILED DESCRIPTION OF THE DISCLOSED EMBODIMENT

Figure 1:
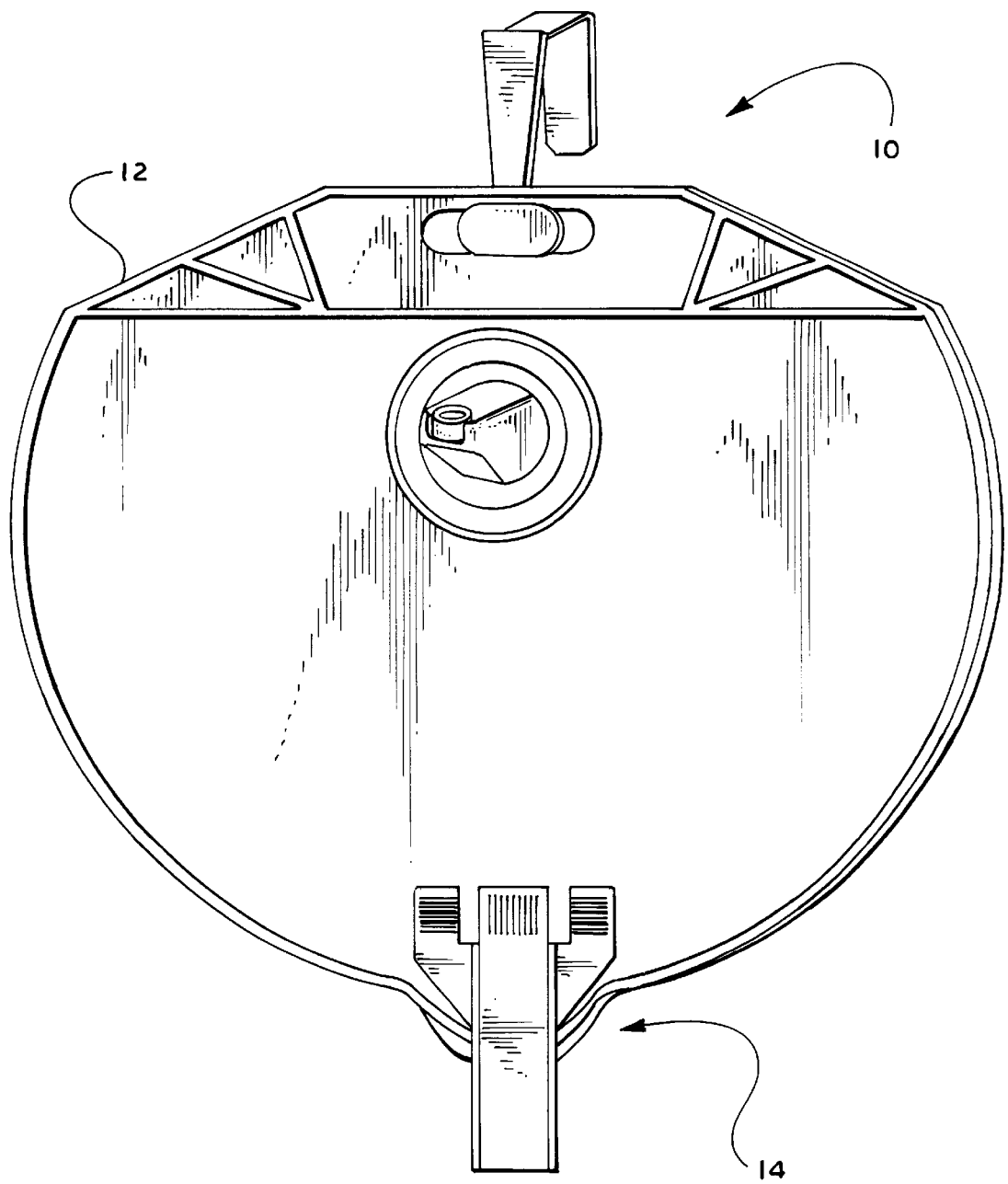
FIG. 1 is a front view of a urine collection container with lever-style drain assembly according to the present invention.

Referring now to the drawings, in which like numerals indicate like elements throughout the several views, FIG. 1 shows a urine collection container 10, including a collection bag 12 and drain assembly 14. The bag 12 is of conventional design and consists of front and back sheets of a flexible, impermeable plastic such as polyvinyl chloride, heat welded around their peripheries to form a central collection chamber therebetween.

The drain assembly 14 consists of five components: an outlet port 18, an outlet tube 20, a housing 22, a lever 23, and a cover member 24. Each of these components will now be discussed in more detail.

Figure 2:
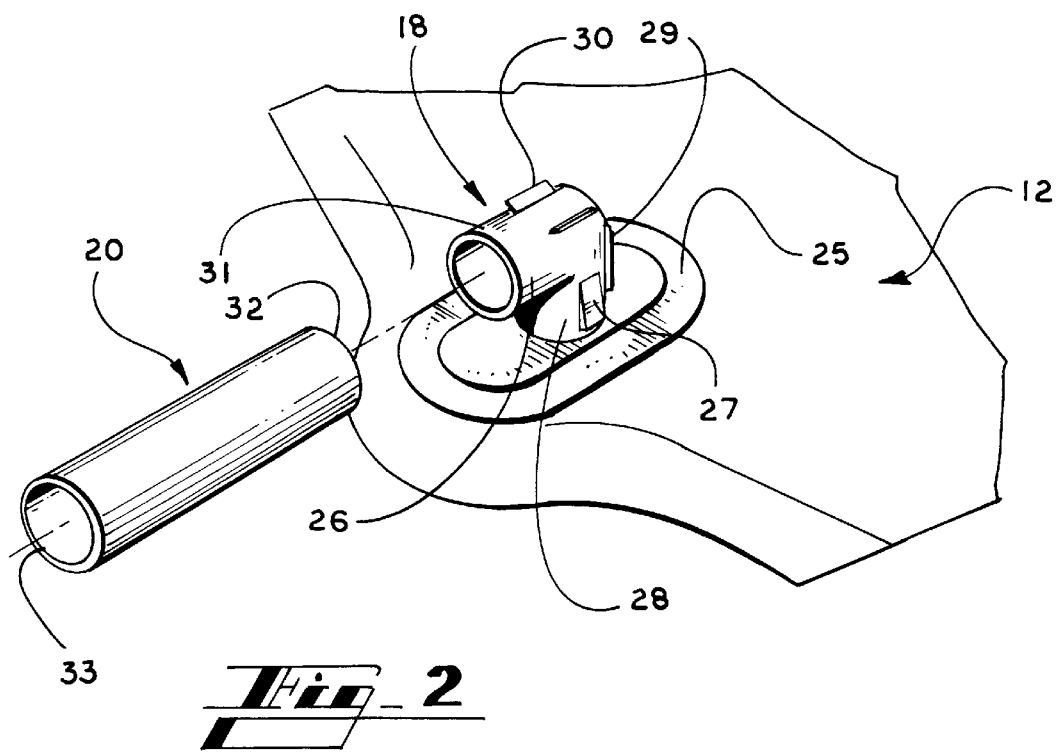
FIG. 2 is a perspective view of an outlet port of the drain assembly of FIG. 1 with an outlet tube shown in exploded relation.

With reference to FIG. 2, the outlet port 18 is a molded plastic component which is welded to the lower portion of the bag 12 overlying a hole (not shown) in the front face of the bag. The outlet port 18 has a base 25 which is mounted to the front face of the bag 12. An L-shaped duct or elbow 26 projects forward from the base 25 and then downward. An opening is formed through the base 25 of the outlet port 18 and extends the length of the elbow 26. Ears 27 are formed along the lateral sides of the forward projecting leg 28 of the elbow 26, the rear edges of the ears 27 being spaced apart from the base 25 of the outlet port 18. Upward projecting ridges 29 are formed along the upper surface of the forward projecting leg 28 of the elbow 26. Vertical stops 30 are formed on the downward extending leg 31 of the elbow 26. The lower edge of each stop 30 is generally aligned with the lower edge of the forward projecting leg 28 of the elbow 26.

Referring further to FIG. 2, the outlet tube 20 is a short length of flexible, resilient tubing which has an inner diameter which is slightly smaller than the outer diameter of the lower end of the elbow 26 of the outlet port 18. The outlet tube 20 has an upper end 32 and a lower end 33. The upper end 32 of the outlet tube 20 is stretched over the lower end of the elbow 26 and is held in place by a friction fit. The outlet tube 20 is thus in fluid communication with the interior of the bag 12 by way of the outlet port 18.

Figure 3:
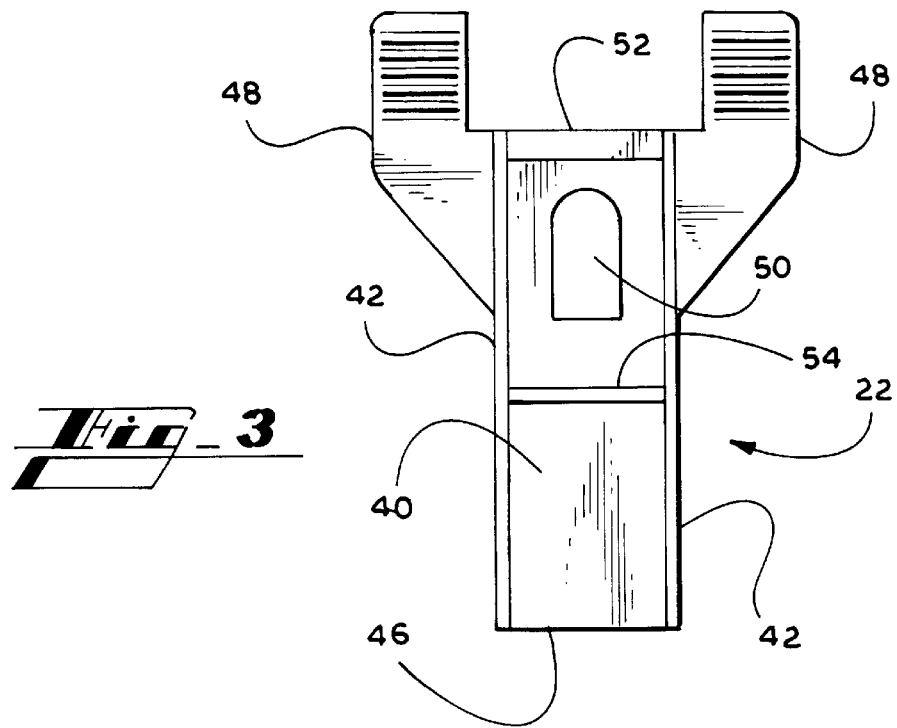
FIG. 3 is a front view of a housing of the drain assembly of FIG. 1.

Referring now to FIGS. 3 and 4, the housing 22 comprises a back panel 40 and two side panels 42 which project forward from the lateral edges of the back panel. The housing has an open front 44 and an open lower end 46. A pair of finger-receiving flanges 48 extend upward and outward from the side walls of the housing. The front and back surfaces of the finger-receiving flanges 48 are grooved or otherwise textured to provide a non-slip surface. An opening 50 is formed in the back panel 40. A lip 52 is formed at the upper end of the housing 22. A stop 54 projects forward from an intermediate location on the back panel 40.

Referring now to FIG. 5, the lever 23 has a width approximately equal to the width of the open front 44 of the housing 22 and a height which is taller than the open front of the housing. A pair of follower pins 60 extend from opposite sides of the lever 23 at a location spaced slightly above the lower end of the lever. A finger-receiving portion 62 is formed at the upper end of the lever and is grooved, knurled or otherwise textured to provide a non-slip surface. A hook 64 extends rearward from the lever 23 adjacent its upper end. A closure member 66 extends rearward from an intermediate location on the lever 23.

With reference to FIG. 6, the cover member 24 comprises a generally rectangular panel 75 having a width and depth dimensioned to fit closely within the open lower end 46 of the housing 22. Upstanding flanges 76 are located at either lateral edge of the panel 75. An elongated slot 78 is formed in each upstanding flange 76.

FIG. 7 shows the lever 23 and cover member 24 mounted to the housing 22. The lower end of the lever 23 is pivotably mounted to the lower front edge of the housing 22 by way of a pivot pin 80. In a closed position, the lever 23 fits within the open front 44 of the housing 22 with the hook 64 adjacent the upper end of the lever engaging the lip 52 at the top of the housing to retain the lever in a closed position. The cover member 24 is pivotably mounted to the housing 22 at pivot points 82 on each upstanding flange 76 spaced upward from the panel 75. The pivotable mounting can be accomplished in any conventional manner, such as by inwardly projecting pins extending from the inner surfaces of the side walls of the housing which engage corresponding holes in the flanges of the cover member, by outwardly projecting pins on the flanges of the cover member which engage corresponding holes in the side walls of the housing, or by mutually aligned holes in the housing side walls and the flanges which receive a separate pivot pin. With the cover member 24 thus pivotably mounted to the housing 22, the follower pins 60 projecting outward from the lateral edges of the lever 23 are received within the elongated slots 78 in the upstanding flanges 76 of the cover member.

Operation of the device will now be described with reference to FIGS. 7 and 8. Referring first to FIG. 7, when the lever 23 is in its closed position, the hook 64 at the upper end of the lever engages the lip 52 at the upper end of the housing 22 to maintain the lever in its closed position. The closure member 66 extending rearward from the inner face of the lever 23 compresses the outlet tube 20, clamping off the lumen of the outlet tube and preventing fluid flow. The follower pins 60 of the lever 23 abut the upper ends of the elongated slots 78 of the cover member 24, retaining the cover member in its closed position and thereby preventing accidental contact by healthcare personnel with the lower end of the outlet tube 20.

To open the drain assembly 10 to empty the bag or to collect a sample for analysis, the operator places a finger behind the upper end of the lever 23. Placing one or more other fingers on the finger-receiving flanges 48 at the upper end of the housing 22 to gain leverage, the user pulls the upper end of the lever 23 outward, as shown in FIG. 8. The hook 64 at the upper end of the lever 23 disengages from the lip 52 at the upper end of the housing 22, and the upper end of the lever pivots outward and downward. As the lever 23 pivots, the follower pins 60 on the lever ride within the elongated slots 78 of the cover member 24 and cause the cover member to pivot outward and upward, exposing the discharge end of the outlet tube 20 at the lower end of the housing 22. In addition, as a lever 23 pivots, the closure member 66 disengages from the outlet tube. The outlet tube 20 opens under its own resiliency and the fluid pressure exerted by the contents of the bag 12, and fluid is discharged.

When the bag 12 has been emptied, or when a sufficient amount has been drawn off for analysis, the user places his fingers behind the finger-receiving flanges 48 of the housing 22, places his thumb on the finger-receiving portion at the front upper end of the lever 23, and pivots the lever upward and inward to the position shown in FIG. 7. As the lever 23 closes, the follower pins 60 on the lever cause the cover member 24 to pivot downward and rearward, covering the lower end of the housing 22 to prevent accidental contact with the discharge end of the outlet tube. Simultaneously the closure member 66 once again compresses the outlet tube 20, clamping off the lumen to prevent fluid flow. The hook 64 at the upper end of the lever 23 snaps behind the lip 52 at the upper end of the housing 22 to lock the lever in the closed position.

The use of follower pins 60 on the lever 23 riding within elongated slots 78 on the cover member 24 presents a reliable, inexpensive linkage between the lever and the cover member which effects movement of the cover member in conjunction with the operation of the lever. However, it will be appreciated by those skilled in the art that many other forms of linking the lever 23 with the cover member 24 may provide satisfactory results, such as gears, cams, cables and pulleys, and the like.

An alternate embodiment of a drain assembly 110 shown in FIGS. 9 and 10 attains a mechanical advantage by coupling a lever 123 to a cover member 124 at a location below the pivot point of the lever. A housing 122 is mounted over an outlet port 18 and outlet tube 20 in the same manner as previously described with respect to the drain assembly 10. The lever 123 is pivotably mounted to the housing 122 at a pivot point 125 which is located at an intermediate point on the lever. The lever 123 includes a downward extending arm 126 which extends below the pivot point 125. Follower pins 127 extend laterally from the lower end of the downward extending arm 126.

The cover member 124 is pivotably mounted to the housing 122 at a pivot point 128. An elongated slot 130 is formed at the forward end of the cover member 124 at a location forward of the pivot point 128. The follower pins 127 of the lever 123 engage the elongated slot 130 at the forward end of the cover member 124 to pivotably and slidably couple the forward end of the cover member to the downward extending, arm 126 of the lever.

When the lever 123 is in its closed position, as shown in FIG. 9, a closure member on the inner surface of the lever compresses the outlet tube 20 in the same manner as previously described with respect to the drain assembly 10. The cover member 124 is closed, preventing accidental contact by the operator with the lower end of the outlet tube 20.

When the lever 123 is opened, the downward extending arm 126 pivots inward, as illustrated in FIG. 10. The forward end of the cover member 124, slidably and pivotably coupled to the arm 126, also pivots upward and inward, causing the major portion of the cover member to pivot downward and forward, uncovering the lower end of the housing 122. As the lever moves further forward, the closure member on the inner surface of the lever disengages from the outlet tubing, permitting the tubing to open and allowing fluid to be discharged through the lower end of the tubing and out of the lower end of the housing.

The levers 23, 123 are designed so that as they are closed, the flexible outlet tube 20 is compressed beyond the point needed to occlude the lumen of the tube. The reason for this design is that as the levers 23, 123 are opened, the levers can be rotated a short distance with the tube 20 still remaining closed. This rotation gives the cover member 24, 124 the opportunity to rotate away from the opening at the lower end of the housing 22, 122, so that by the time the outlet tube 20 opens and fluid begins to be discharged, the cover member is out of the way.

The present invention provides a number of advantages. The housing 22 can be grasped with one hand while a finger of that hand moves the lever 23 to open or to close the drain, thereby permitting one-handed operation. Further, since the outlet tube 20 is essentially fixed with respect to the housing 22, the user can control the direction of fluid discharge as they hold the housing. Also, because the pivoting action of the lever 23 is intuitive, ease of operation is enhanced.

Another advantage of the disclosed embodiments is that the device is operated from a location which is spaced apart from the discharge end of the outlet tubing 20. Because the levers 23, 123 are manipulated from their upper ends, even when the cover members 24, 124 are retracted to discharge the contents of the bag, the operator's fingers are not in the proximity of the discharge. Possibility of accidental contamination is therefore reduced.

Another advantage of the disclosed embodiments is that retracting the cover member and opening the drain assembly are both achieved in a single step, just as closing the drain assembly and deploying the cover member are achieved in a single step.

Yet another advantage of the disclosed embodiments is that when the hook 64 of the lever 23 engages the lip 52 of the housing 22, it snaps into place, causing vibrations which can be felt by the operator. Further, the snapping action creates an audible "click" sound, which can be heard by the operator. The tactile and audible confirmations can be very advantageous in a hospital environment, where the operator may be working in darkened or dimly lit rooms, or where the bag may be hung well below eye level such that the operator cannot easily see the visual indicators.

Finally, it will be understood that the preferred embodiment has been disclosed by way of example, and that other modifications may occur to those skilled in the art without departing from the scope and spirit of the appended claims.

What is claimed is:

1. A fluid collection bag and drain assembly, comprising:
   a container having an interior chamber for collecting fluid;
   a compressible, resilient outlet tube mounted to said container, said outlet tube having a discharge end and having a passage in fluid communication with said interior chamber of said container;
   a housing surrounding said outlet tube and having an open lower end, said discharge end of said outlet tube being disposed to discharge fluid through said open lower end;
   a lever pivotably mounted to said housing, said lever having a closure member operative to clamp off said outlet tube when said lever is in a closed position and to permit said outlet tube to open when said lever is in an open position;
   a cover member pivotably mounted to said housing and normally operative to close said open lower end of said housing, said cover member being operatively linked to said lever such that when said lever is opened, said cover member is opened to uncover said open lower end of said housing concurrent with said outlet tube being permitted to open, whereby said cover member prevents accidental contact with said discharge end of said outlet tube when fluid is not being discharged from said container.

2. The fluid collection bag and drain assembly of claim 1, wherein said lever further comprises at least one pin extending therefrom, wherein said cover member includes means defining a slot therein, and wherein said cover member being operatively linked to said lever comprises said pin of said lever riding within said slot of said cover member.

3. The fluid collection bag and drain assembly of claim 1, wherein said lever is pivotably mounted to said housing at a pivot point located at a lower end of said lever, and wherein said cover member is operatively linked to said lever at a location on said lever spaced upward from said pivot point.

4. The fluid collection bag and drain assembly of claim 1, wherein said lever is pivotably mounted to said housing at a pivot point located at an intermediate location on said lever, and wherein said cover member is operatively linked to said lever at a location on said lever spaced downward from said pivot point.

5. The fluid collection bag and drain assembly of claim 1, wherein said closure member of said lever compresses said outlet tube more than is necessary to occlude said passage of said outlet tube, such that when said lever is opened, said outlet tube remains occluded during a first portion of movement of said lever.

6. The fluid collection bag and drain assembly of claim 1, further comprising at least one finger-receiving flange fixedly mounted to said housing adjacent the location of said upper end of said flange when said flange is in said closed position, whereby a user can exert leverage against said finger-receiving flange to facilitate movement of said lever.

* * * * *